(12) United States Patent
Odermatt et al.

(10) Patent No.: US 8,460,703 B2
(45) Date of Patent: Jun. 11, 2013

(54) COMBINATION FOR AN ADHESIVE BONDING OF BIOLOGICAL TISSUES

(75) Inventors: Erich Odermatt, Schaffhausen (CH); Jürgen Wegmann, Stockach (DE); Katrin Sternberg, Rostock (DE); Detlef Behrend, Warnemünde (DE)

(73) Assignees: Aesculap AG (DE); Universität Rostock (DE)

( * ) Notice: Subject to any disclaimer, the term of this patent is extended or adjusted under 35 U.S.C. 154(b) by 331 days.

(21) Appl. No.: 12/671,947

(22) PCT Filed: Aug. 1, 2008

(86) PCT No.: PCT/EP2008/006348
§ 371 (c)(1),
(2), (4) Date: Nov. 3, 2010

(87) PCT Pub. No.: WO2009/018967
PCT Pub. Date: Feb. 12, 2009

(65) Prior Publication Data
US 2011/0040323 A1 Feb. 17, 2011

(30) Foreign Application Priority Data
Aug. 3, 2007 (DE) .................. 10 2007 038 125

(51) Int. Cl.
*A61K 7/075* (2006.01)
*A61K 7/08* (2006.01)

(52) U.S. Cl.
USPC .............................. 424/461; 424/462; 514/62

(58) Field of Classification Search
USPC ................. 424/461, 462, 497, 479, 488
See application file for complete search history.

(56) References Cited

U.S. PATENT DOCUMENTS

| | | | |
|---|---|---|---|
| 4,740,534 A | 4/1988 | Matsuda et al. | |
| 4,804,691 A | 2/1989 | English et al. | |
| 5,569,725 A * | 10/1996 | Carroll et al. | 525/454 |
| 6,558,790 B1 * | 5/2003 | Holguin et al. | 428/355 R |
| 2004/0013626 A1 | 1/2004 | Gref et al. | |
| 2005/0002893 A1 * | 1/2005 | Goldmann | 424/70.27 |
| 2007/0148215 A1 | 6/2007 | Teslenko et al. | |
| 2009/0227779 A1 | 9/2009 | Qian et al. | |
| 2009/0280179 A1 | 11/2009 | Neumann et al. | |
| 2009/0318584 A1 | 12/2009 | Speitling et al. | |

FOREIGN PATENT DOCUMENTS

| | | |
|---|---|---|
| EP | 1 498 128 A1 | 1/2005 |
| EP | 1 719 530 A2 | 11/2006 |
| WO | 96/03159 A1 | 2/1996 |
| WO | 98/19718 A1 | 5/1998 |
| WO | 03/035122 A1 | 5/2003 |
| WO | 2005/118011 A1 | 12/2005 |
| WO | 2006/069578 A1 | 7/2006 |
| WO | 2007/090373 A2 | 8/2007 |

* cited by examiner

*Primary Examiner* — Fereydoun G Sajjadi
*Assistant Examiner* — Yanzhi Zhang
(74) *Attorney, Agent, or Firm* — DLA Piper LLP (US)

(57) ABSTRACT

A composition for the adhesive bonding and/or fixing of biological and/or synthetic tissues includes the components:
a) a nitrogen-functionalized polysaccharide; and
b) a terminally functionalized oligolactone.

21 Claims, 8 Drawing Sheets

COMBINATION FOR AN ADHESIVE BONDING OF BIOLOGICAL TISSUES

RELATED APPLICATIONS

This is a §371 of International Application No. PCT/EP2008/006348, with an international filing date of Aug. 1, 2008 (WO 2009/018967 A2, published Feb. 12, 2009), which is based on German Patent Application No. 10 2007 038 125.7, filed Aug. 3, 2007, the subject matter of which is incorporated by reference.

TECHNICAL FIELD

This disclosure relates to a combination in the form of a medicinal adhesive composition which is suitable for the adhesive bonding and/or fixing of biological and/or synthetic tissues.

BACKGROUND

Modern wound closure techniques are increasingly based on the use of so-called "tissue" adhesives. These are usually simple to use. Other advantages result from decreased scar formation during wound healing, less marked hypertrophy and the elimination of postoperative treatments.

At present, various types of tissue adhesives are commercially available. The so-called "fibrin" adhesives mainly consist of plasma proteins, in particular, fibrinogen and thrombin. These adhesives intervene actively in the clotting cascade and as a rule have good hemostatic properties. However, fibrin adhesives are normally produced from human or animal sources. Hence, their preparation is usually time- and above all cost-intensive. A further disadvantage lies in an infection risk to the patients which cannot be entirely excluded.

On the other hand, partly synthetic adhesives, for example, gelatin-resorcinol-formaldehyde, do often have higher adhesive strength than the fibrin adhesives described above. However, as a rule they have poorer hemostatic properties compared to the natural tissue adhesives. In principle, infections can still be transferred via the natural component of a partly synthetic adhesive. In addition, partly synthetic adhesives are often crosslinked with a toxic compound, for example, formaldehyde or glutaraldehyde.

In the meantime, exclusively synthetically produced tissue adhesives have also increasingly come into use. These adhesives are mainly compositions based on cyanoacrylates. At present, various cyanoacrylates are used as surgical adhesives. For example, the adhesive Dermabond® consists of n-octyl 2-cyanoacrylate. A further example is the adhesive product Histoacryl®, which contains n-butyl 2-cyanoacrylate. Tissue adhesives based on cyanoacrylates are usually rapid-curing. The use of cyanoacrylate adhesives does indeed give satisfactory results for surface wound care. However, there are certain concerns from the toxicological point of view concerning the use of cyanoacrylate adhesives for the treatment of internal wounds. A further point is that cyanoacrylate compounds react with biological tissues in a strongly exothermic reaction, owing to which healthy cells in the wound area can suffer lasting damage.

Since partly and also wholly synthetic tissue adhesives are subject to certain limitations in their medical applications, there is a constant search for alternative adhesive compositions. One alternative adhesive composition is, for example, described in EP 1 719 530 A2. However, the compositions disclosed there are slow-curing, owing to which their medical usability is also limited.

A surgical adhesive based on a urethane prepolymer and an unsaturated cyano compound is found in U.S. Pat. No. 4,740,534. The cyano compound can be a cyanoacrylate or a cyanoacrylonitrile. As already mentioned, the use of cyanoacrylate compounds in particular is subject to certain disadvantages.

A further biological adhesive is known from WO 2005/118011 A1. The adhesive composition described there contains a mixture of crosslinkable prepolymers which are modified with isocyanate groups. With this type of adhesive composition, a disadvantage is their comparatively low viscosity, as a result of which, particularly with heavily bleeding wounds, there is the danger of the composition being flushed out of the wound area. This adhesive composition also has a comparatively long gelling or curing time. This can lead to additional complications, particularly with severe hemorrhages.

It could therefore be helpful to provide a combination suitable, in particular, as an adhesive composition for adhesive bonding of biological tissues, which is simple to use and, in particular, is suitable both for internal and also for surface wound treatment.

SUMMARY

We provide a composition for adhesive bonding and/or fixing of biological and/or synthetic tissues including a) a nitrogen-functionalized polysaccharide and b) a terminally functionalized oligolactone.

We also provide a compound including the composition, wherein the polysaccharide is at least partly crosslinked with the oligolactone.

We further provide a medical equipment product including the composition.

We further yet provide a kit including at least two separate containers, wherein one container contains a nitrogen-functionalized polysaccharide and the other container a terminally functionalized oligolactone.

We also further provide a kit including the nitrogen-functionalized polysaccharide and/or terminally functionalized oligolactone.

We still further provide an in vitro process for adhesive bonding including contacting components of the composition with one another and with at least one substrate to be bonded, which contains reactive functional groups.

BRIEF DESCRIPTION OF THE DRAWINGS

Further features and advantages emerge from the following description of the diagrams and the examples. Individual features can each be implemented in themselves alone or as several in combination with one another.

The figures show the following.

DETAILED DESCRIPTION

Our compositions for adhesive bonding and/or fixing of biological and/or synthetic tissues, comprises the components:

a) at least one, in particular one, nitrogen-functionalized polysaccharide; and b) at least one, in particular one, terminally functionalized oligolactone.

The bonding process of the combination, which is preferably a surgical adhesive combination, is based on a reaction of the components thereof. Particularly advantageously, this is in-situ crosslinking of the nitrogen-functionalized polysaccharides with the terminally functionalized oligolactones. Because of the terminal functionalization, the oligolactones of the combination are suitable and, in particular, reactive crosslinking partners for the polysaccharides. The crosslinking, is in particular, based on covalent bonds. In addition, physical crosslinking processes can also be involved. Through the reaction between the components of the combination, wound closures can be formed which are significantly stronger than, for example, with the use of conventional, clinically tried and tested fibrin adhesives. Moreover, the bonding to the biological tissue is achieved by the reaction of the terminal functional groups of the oligolactones with tissue proteins.

Preferably, the polysaccharide is a naturally occurring polysaccharide. For example, the polysaccharide can be a glycosaminoglycan (mucopolysaccharide). An example of a preferred naturally occurring polysaccharide is hyaluronic acid. The hyaluronic acid can, for example, have a molecular weight of at least 20 kDa (kilodaltons).

In addition or alternatively to the aforesaid polysaccharides, the polysaccharide can be derived from a naturally occurring polysaccharide. In this case, this is typically a chemically modified polysaccharide. In this variant, the nitrogen functionalization of the polysaccharide is based on the chemical modification. Essentially all polysaccharides which are amenable to such functionalization are possible for this.

Furthermore, it is possible for the polysaccharide of the combination to be a completely synthetic polysaccharide.

Particularly preferably, the polysaccharide is a polysaccharide bearing amino groups, in particular, primary amino groups. Preferably, the proportion of monosaccharide units in the polysaccharide which bear an amino group is at least 30%, preferably 80%. The polysaccharide preferably has a molecular weight of 10 to 350 kDa, in particular, ca. 200 kDa.

The polysaccharide may be an at least partly deacetylated glycosaminoglycan. The use of an appropriate glycosaminoglycan derivative is also possible. Possible suitable polysaccharides are, in particular, at least partly deacetylated chondroitin sulfate, keratan sulfate and/or hyaluronic acid.

The polysaccharide may have a deacetylation level between 50 and 98%, in particular, between 60 and 95%, preferably between 80 and 90%.

Particularly preferably, the polysaccharide is a chitosan. The use of chitosan is particularly advantageous owing to its styptic (hemostatic) and, in particular, antimicrobial properties. It can also be provided that the polysaccharide is a chitosan derivative. The chitosan preferably has a molecular weight between 15 and 270 kDa. The chitosan preferably has a deacetylation level of ca. 86%.

The combination may contain several different nitrogen-functionalized polysaccharides. These can, in particular, be contained in the combination in the form of a mixture. Concerning suitable polysaccharides, reference is made to the foregoing description.

The terminally functionalized oligolactone preferably serves as a crosslinking agent. "Internal esters" of hydroxycarboxylic acids and, hence, in the extended sense also oligoglycolides, oligolactides and oligolactones of mixed composition, in particular based on glycolide and lactide, are described as oligolactones. These can, for example, be produced by ring-opening polymerization or oligomerization.

Catalysts are preferably used for the production of the oligolactones. The catalysts can in principle be tin compounds. Zinc and/or iron compounds are particularly preferred owing to their good biocompatibility.

Essentially for the terminal functionalization of the oligolactone, all reactive groups, in particular organic groups, are possible. For example, the oligolactone can be terminally functionalized with aldehyde and/or epoxide groups. Preferably, the oligolactone has terminal isocyanate groups. This is particularly advantageous since an appropriate combination with nitrogen-functionalized polysaccharides and oligolactones modified with isocyanate groups reacts to give an adhesive bond with increased bonding strength to substrates to be bonded, in particular, biological tissues.

For the terminal functionalization of the oligolactones, these are preferably reacted with diisocyanates. The oligolactones of the combination are preferably modified with an aliphatic isocyanate group at their end or at their ends. The use of aliphatic diisocyanates, in particular hexamethylene diisocyanate (HMDI) for the functionalization of the oligolactones is particularly preferable since carcinogenic diamines can be formed from aromatic diisocyanates. With a stoichiometric reaction, no purification is necessary. If necessary, however, a purification can be performed. For this, depending on the structure and the thermal stability of the oligolactone produced, distillation is a possibility.

The oligolactone may contain a polyhydric, in particular at least dihydric, alcohol. As suitable alcohols, in particular, ethylene glycol (1,2-ethanediol) and/or glycerin (1,2,3-propanetriol) are possible.

The oligolactone is preferably formed from a polyhydric alcohol and hydroxycarboxylic acids, in particular, glycolic and/or lactic acid. Preferably, at least one hydroxyl group of the polyhydric alcohol is esterified with hydroxycarboxylic acid units, in particular, with lactic and/or glycolic acid units. In the case of a dihydric alcohol, it is particularly preferable if both hydroxyl groups are present in esterified form. The hydroxyl groups of the polyhydric alcohol are preferably, at least partly, esterified with a chain of 1 to 10, in particular 2 to 5, hydroxycarboxylic acid units. With increasing number of units, the viscosity of the oligolactone and of the adhesive obtained during a reaction with the nitrogen-functionalized polysaccharide increases. The oligolactones from polyhydric alcohol and hydroxycarboxylic acid units bear functional groups which constitute the terminal functionalization of the oligolactone at the terminal hydroxycarboxylic acid unit or units.

Preferably, the oligolactone is an ethylene glycol oligolactide (EOL). Apart from this, other oligolactones, in particular, ethylene glycol oligoglycolide (EOG 1/2, M=294.2 g/mol), pentaerythritol oligolactide (POL 1/4 M=712.6 g/mol), glycerol oligolactide (GOL 1/0.5, M=164.1 g/mol) and glycerol oligolactide-co-glycolide (GOLG 1/1/3, M=584.4 g/mol) can be used.

The combination can further contain several different oligolactones, in particular, in the form of a mixture. Concerning the possible oligolactones, reference is made to the statements made above.

If a rapid reaction of the components of the combination and, hence, rapid bonding is desired, a catalyst for the reaction between the nitrogen-functionalized polysaccharides and the terminally functionalized oligolactones can be used as a further component in the context of the combination. Through the use of such a catalyst, the reaction of the hydroxyl groups of the polysaccharides, and also or mainly the amino groups in the case of polysaccharides bearing amino groups, with the terminal functional groups of the oligolactones can be greatly accelerated. A catalytic acceleration of the reaction between the components can above all be useful for medical uses. For example, with particularly heavily bleeding wounds the use of a catalyst can be desirable, whereas in the adhesive bonding of bones a slower curing of the combination can make sense, to enable adjustment with the possibility of a subsequent correction.

Possible suitable catalysts are, in particular, amines, amidines, more advantageously 2,3-dimethyl-3,4,5,6-tetrahydropyrimidine, a tertiary amine, more advantageously triethylamine, tributylamine, dimethylbenzylamine, N-methyl-, N-ethyl- or N-cyclohexylmorpholine, N,N,N',N'-tetramethylethylenediamine, N,N,N',N'-diaminoethyl ether, bis(dimethylaminopropyl)urea, dimethylpiperazine, 1,2-dimethylimidazole, 1-aza-bicyclo-(3,3,0)-octane and preferably 1,4-diaza-bicyclo-(2,2,2)-octane and/or an alkanolamine, such as triethanolamine, triisopropanolamine, N-methyl- and N-ethyldiethanolamine and dimethylethanolamine, preferably 1,4-diaza[2.2.2]bicyclooctane (Dabco).

Preferably, the content of the polysaccharide in the combination is 1 to 80 wt. %, in particular 5 to 70 wt. %. The oligolactone content in the combination is preferably 20 to 99 wt. %, in particular 30 to 95 wt. %. The percentage contents by weight are based on the total mass of the combination without solvent.

By variation of the polysaccharide and/or oligolactone content in the combination, the adhesive or bonding strength of the adhesive bond resulting from the combination after reaction of the components thereof can be adapted in a particularly advantageous manner to the particular use purpose. Thus, in particular, a higher degree of crosslinking after mixing with the polysaccharide can be achieved by a higher oligolactone content. Also, through a higher oligolactone content in the combination, reactive hydroxyl and/or amino groups from the substrate to be bonded, in particular biological tissues can be more strongly incorporated into the crosslinking, as a result of which the adhesive strength (bonding strength or holding strength) increases overall.

The polysaccharide and/or the oligolactone may be dispersed, preferably dissolved, in one or more solvents. The solvent is preferably water. Further, organic solvents, which are advisedly biologically compatible, can also be used. A suitable solvent is dimethyl sulfoxide (DMSO). Preferably, the solvent is a solvent mixture of DMSO and water.

The oligolactone may be present in the form of an organic solution, preferably a DMSO solution, in particular with an oligolactone content between 50 and 99 wt. %, in particular 70 and 90 wt. %, preferably of ca. 80 wt. %, based on the total weight of the solution.

Preferably, the polysaccharide and the oligolactone are present separately from one another. Polysaccharide and oligolactone are advantageously only mixed when a reaction between them is desired. The combination may already be contained in an application device. For example, the components can be present separately from one another in individual cartridges which are preferably located in a mixing unit. Preferably, the polysaccharide and the oligolactone are present separately from one another in the chambers of a multicomponent syringe, in particular, a two-component or double chamber syringe, for example, of the Mixpack type (Mixpack Systems AG, Rotkreuz, Switzerland). The multicomponent syringe advantageously has a mixing extruder for the mixing of the components of the combination, initially present separately from one another.

It is further preferred that the combination is contained in a spray device. The spray device can also have at least two chambers. As a result, the components of the combination, in particular the polysaccharide and the oligolactone, can particularly advantageously be kept separate from one another until their actual use.

A reaction, preferably crosslinking, of the components can be initiated or started after their mixing on a substrate to be bonded within a period of <100 seconds, in particular <80 seconds, preferably <60 seconds.

The polysaccharide may be present in the form of an aqueous dispersion, in particular, aqueous solution. The polysaccharide is preferably present in the form of an aqueous solution with a polysaccharide content of 2 to 5 wt. %, preferably 3 to 4 wt. %, based on the total weight of the solution.

The combination may contain additives, auxiliary agents and/or fillers. The additives and/or auxiliary agents can be antimicrobial, in particular, antibiotic, active substances. The fillers can, for example, be gelatin, collagen and/or albumin. The use of gelatin and/or collagen has the further advantage that these compounds also have hemostatic properties. Preferred fillers, in particular for the adhesive bonding of hard tissues, are selected from the group dicalcium phosphate, tricalcium phosphate and hydroxyapatite. In the case of tricalcium phosphate, this can, in particular, be β-tricalcium phosphate. Carbonates, for example, calcium carbonate, and oxide materials, for example, silicon dioxide, are further examples of possible fillers. Finally, the additives or auxiliary substances can also be growth factors, inflammation-inhibiting, disinfecting and/or antimicrobial compounds.

It can of course be provided that the combination consists of the nitrogen-functionalized polysaccharide and the terminally functionalized oligolactone, and optionally also of at least one additive or auxiliary substance. Concerning this, reference is made to the foregoing description.

The polysaccharide and/or the oligolactone may be present in sterilized form. The components of the combination can, for example, be present separately from one another in individual cartridges. The cartridges can advantageously be located in a mixing unit. Preferably, the components are sterile packed, in particular, in a multicomponent syringe, preferably with a fitted mixing extruder. Sterilization of the combination or of its individual components can advantageously be achieved without structural changes. This can, for example, be effected by sterile filtration of suitable solutions. Preferably, the combination comprises a solution of the nitrogen-functionalized polysaccharide, the solution of the polysaccharide being sterilized by steam sterilization. The terminally functionalized oligolactones are preferably converted into a sterilized form by γ-sterilization. In principle, aseptic filling of the components of the combination is also possible. However, both the steam sterilization and also the sterilization by γ-radiation can with particular advantage be effected on the already packed combination. Moreover, the combination can be present in packaged form.

Particularly preferably, the combination is present as an adhesive composition.

The combination is particularly suitable for the adhesive bonding and/or fixing of biological tissues, where the tissues to be adhesively bonded are preferably hard and/or soft tissues. The hard tissue to be adhesively bonded can, in particular, be bone tissue, for example, in the form of bone cavities, and/or tooth extractions. The soft tissues to be adhesively bonded can, in particular, be organs, blood vessels and/or parenchymal tissue. Possible organs are, in particular, liver, kidneys, spleen and/or lungs.

Furthermore, the combination can be used for the fixing and/or sealing of implants, in particular, hernia meshes, vascular prostheses, catheters, stents and/or replacement materials for the dura mater. One possibility, for example, is the fixing of a hernia mesh to the abdominal wall. The dura mater replacement material to be fixed can, in particular, be a bovine pericardium. Through the use of the combination, suturing of the replacement material is not necessary. Hence, time and treatment costs can be saved.

A further advantageous use of the combination is the sealing of anastomoses and/or wound dressings (patches) on hollow organs, for example, blood vessels. The combination can also be used for the fixing of so-called "drug delivery devices" and, in particular, of porous carrier structures and/or membranes for potential use in regenerative medicine (tissue engineering).

A further use field of the combination is wound cleaning of particularly infected wounds. In principle, use of the combination in plastic, reconstructive and/or cosmetic surgery is conceivable, in particular, for the avoidance of scarring, which is mainly caused in the suturing of wounds.

Particularly preferably, the combination is used for the closure or for the stoppage or sealing of liquid and/or air leakages in the human and/or animal body. For example, the combination can be used for the sealing of pulmonary leakages, intestinal leakages, bladder leakages, ureter leakages, pericardia, intestinal and/or vascular anastomoses. In addition, the combination is also suitable for sealing puncture channel hemorrhages in vascular surgery and for sealing in arterial bypass operations. The adhesive bond arising by the crosslinking of the combination preferably has elastic properties, which is advantageous, in particular, with markedly expanding tissues, for example, the pulmonary tissue, but also with pulsating tissues, for example, blood vessels.

The combination can be used for the stoppage of minimally invasive hemorrhages. The application is advantageously effected with a trocar. A use of the combination for the filling of tooth extraction voids and/or bone defects can also be envisaged.

In addition or alternatively to the possible uses so far described, the combination can be used for the fixing of muscles, ligaments and/or tendons to bones. The combination can moreover be used for the adhesive bonding of wound borders. Treatment of surgically produced wounds, for example, after a tumorectomy, is possible with the combination.

Furthermore, the combination also enables use in particularly severe cases, in particular, in the treatment of chronic wounds. With such wounds, after the necessary surgical treatment, a severe tensile stress arises, which usually renders wound healing difficult. Even in these cases, the high strength of the wound closure enables a strong seal and, in particular, prevents wound infections. After completion of the crosslinking reaction, compressive dressings can be, for example, used on the wounds thus closed to prevent edema formation.

We also provide a compound in which the components of the combination are mixed and the nitrogen-functionalized polysaccharides are at least partly crosslinked via the terminally functionalized oligolactones. As already mentioned, the crosslinking can, in particular, be based on covalent bonds, but physical crosslinking is also possible. Preferably, reactive functional groups, in particular, hydroxyl and/or amino groups, of substrates to be adhesively bonded are also incorporated in the crosslinking of the compound. The compound advantageously has good biocompatibility.

Thus, an adhesive composition which contains the combination, i.e., the components a) and b), is also a subject of this disclosure. In other words, this disclosure also relates to an adhesive composition, in particular, for the adhesive bonding and/or fixing of biological and/or synthetic tissues, comprising the components a) at least one, in particular one, nitrogen-functionalized polysaccharide and b) at least one, in particular one, terminally functionalized oligolactone.

Regarding further details and features, reference is therefore made to the foregoing and also the following description.

One advantage of the adhesive formed by reaction of the combination is its biological degradability. Through the cross-linking of the nitrogen-functionalized polysaccharides via the terminally functionalized oligolactones, a very strong adhesive bond is formed, which can ideally be absorbed in the course of the healing process. Here in particular the initial curing phase, associated with high adhesive properties, and the time-dependent, slow absorption in the body when the healing processes have progressed are of particular advantage. Preferably, the adhesive is absorbed (biologically degraded) during a period of about 1 year, preferably during a period of 2 to 6 months. The mechanism of the absorption can, for example, be based on hydrolytic and/or enzymatic processes. In particular, the nitrogen-functionalized polysaccharides can be cleaved and individual fragments thereof transported away and excreted. Alternatively, the fragments, in particular monosaccharides, can also be taken up into cells.

Further, we provide a medical equipment product, in particular for adhesive bonding and/or fixing of biological and/or synthetic tissues, which contains the combination. The medical equipment product is preferably an implant, for example, a hernia mesh. Further, the medical equipment product can also consist of replacement materials, in particular, for closure and/or sealing of the dura mater. In addition, the medical equipment product can be a dental implant, in particular, for the filling of tooth extraction voids. It is also possible that the medical equipment product is a bone implant, in particular, for the treatment and/or filling of bone defects.

Preferably, the medical equipment product is a hemostyptic (styptic agent or hemostatic agent). The medical equipment product is preferably suitable for the closure of internal bleeding and external bleeding wounds. After mixing of its components, the combination particularly advantageously forms a pasty and, in particular, adhesive mass, which, for example, after application to a wound area to be treated constitutes a kind of physical barrier for body fluids, in particular, blood and/or exudate. Particularly advantageously, an outflow of the blood from the wound area is thereby prevented, as a result of which blood platelets and, in particular, clotting factors are concentrated. This advantageously leads to accelerated hemostasis in the wound area.

Preferably, it is a medical equipment product for the adhesive bonding of soft tissue. As already mentioned, soft tissues include mainly organs, blood vessels and/or parenchymal tissue. The use of the medical equipment product for the adhesive bonding of ruptures of various organs, for example, the liver, the kidneys and/or the spleen, is particularly preferred. Further, the medical equipment product can be used for the closure of leakages, in particular, pulmonary leakages. The pasty mass formed by mixing of the components of the combination advantageously possesses high elasticity, which is particularly advantageous with markedly expanding tissues.

The medical equipment product may be suitable for the adhesive bonding of hard tissue, in particular, bones. For the adhesive bonding of bones and for rapid integration of implants, in particular, in the region of the bones, the acceptance of the implanted material by the bone cells is of particular importance. This of course also applies to the adhesives used. Through rapid colonization with osteoblasts and their subsequent maturation, new bone form ation can be promoted and the healing process sometimes considerably shortened. Hence, the medical equipment product is advantageously an implant with a microstructured surface, wherein the combination advantageously acquires this surface structure and, in particular, supports the formation of new bone. Furthermore, use in complex fractures is also possible. Thus, for example, by means of the medical equipment product, bone splinters can be reinserted. Further, the medical equipment product is preferably suitable for the fixation of comminuted fractures, for example, in the facial-cranial region or the extremities, particularly in radial head fractures.

We further provide a kit, in particular, for adhesive bonding, comprising at least two, preferably two, containers. One container contains a nitrogen-functionalized polysaccharide and the other container a terminally functionalized oligolactone. The containers of the kit are preferably the chambers of a multicomponent syringe, in particular, a two-component or twin syringe. The syringe advantageously has a mixing extruder for the mixing of the polysaccharide and the oligolactone. Further, the containers can also be components of a spray applicator or a spray device. Regarding further details and features, in particular regarding the polysaccharide and or the oligolactone used, reference is made to the foregoing description.

In a further aspect, we provide an in vitro or in vivo method for adhesive bonding, wherein the components of the combination are brought into contact with one another and with at least one, preferably at least two, substrate to be adhesively bonded which has reactive functional groups. The functional groups of the substrates to be adhesively bonded are preferably hydroxyl and/or amino groups. In the adhesive bonding process, the bonding of the substrate preferably takes place through a crosslinking of hydroxyl and/or if appropriate amino groups of the nitrogen-functionalized polysaccharides and the substrates by the oligolactones.

At least one of the substrates is preferably an organ, tissue, tooth compartment and/or bone. Possible tooth compartments are, in particular, enamel and/or dentine. Preferably, the substrates are wound borders which have to be adhesively bonded. However, they can also, for example, be inorganic or organic substrates to be adhesively bonded to one another, which are not tissue, for example, plastic or ceramic surfaces. The bonding process can, in particular, be effected in an aqueous medium.

Moreover, it is possible to use as substrates not only macroscopic substrates, but also other reagents which preferably contain hydroxyl and/or amino groups. These can be bonded to on another, but also to solid carriers. Examples of conceivable substrates are low molecular weight compounds, in particular, peptides, and/or cells. Regarding other possible substrates, reference is made to the foregoing description.

Finally, we provide the use of the combination for the production of a medical equipment product. Regarding further details and features concerning the medical equipment product, reference is made to the foregoing description.

A combination preparation is particularly advantageously provided, which is usable in many ways, in particular, in the medical field. As already mentioned, the combination is suitable, in particular, for the adhesive bonding of external and internal wounds. The combination is also suitable for the treatment of heavily bleeding wounds and/or those which have become chronic. Particularly advantageously, the viscosity and fluidity of the combination can be adapted depending, for example, on the length of the wound to be adhesively bonded and, in particular, the wound cleft depth or the substrates to be adhesively bonded. This can be influenced, for example, by the nature of the polysaccharides and/or the oligolactones, in particular, by their length (number of esterified hydroxycarboxylic acid units). In addition, these parameters can be influenced by the selection of a solvent or a solvent mixture, wherein the nature of the solvent is also important. As well as or alternatively to this, additives, for example, thixotropic agents, in particular nanodispersed calcium phosphates (e.g., β-tricalcium phosphate) or nano-dispersed silicic acids can be used for the adaptation of the viscosity and fluidity.

Figure 1:
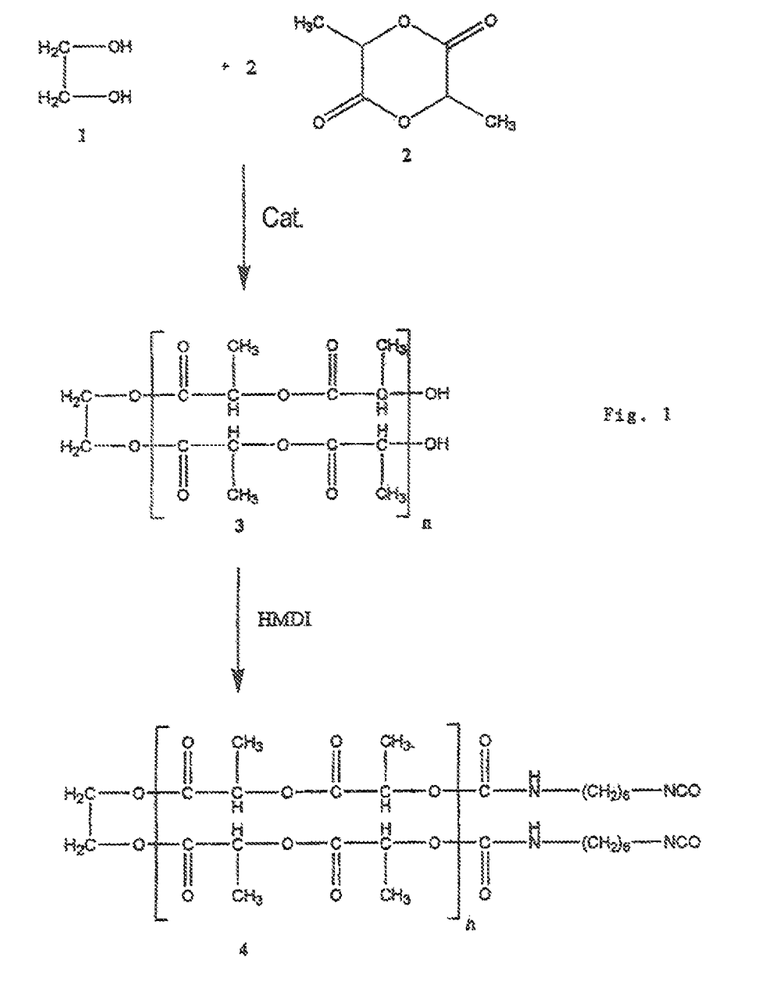
FIG. 1: reaction schemes for preparation of EOL-NCO.
Figure 2:
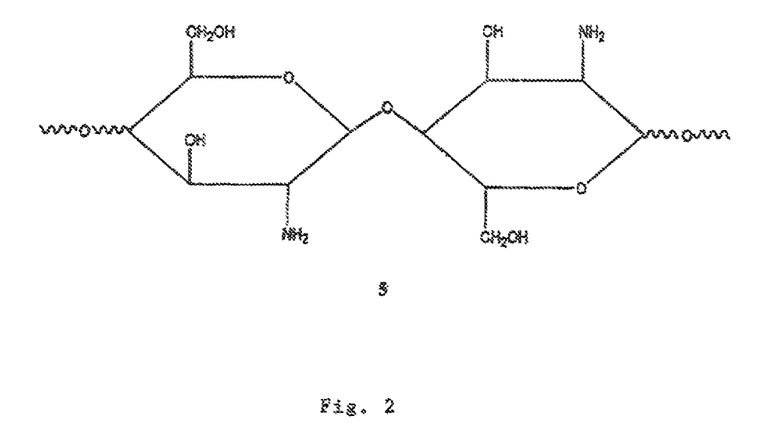
FIG. 2: details from a chitosan molecule.

FIG. 1 shows the preparation of ethylene glycol oligolactide (EOL) 4 which is modified with isocyanate groups at its terminal lactic acid units (EOL-NCO). The synthesis is effected starting from ethylene glycol 1 and cyclic lactides 2, wherein the hydroxyl groups of 1 are esterified with the lactides 2 by a ring-opening oligomerization, and optionally also ring-opening polymerization. For the terminal functionalization of the ethylene glycol oligolactide (EOL) 3 deriving from this, the terminal hydroxyl groups thereof are modified with hexamethylene diisocyanate (HMDI) with the formation of the terminally functionalized oligolactide 4. The oligolactide 4 can now be used as a crosslinking agent for nitrogen-functionalized polysaccharides, for example, for a chitosan 5, the structure whereof is indicated schematically in FIG. 2, and substrates to be adhesively bonded. In FIG. 1, n can, for example, be 1, 2, 3, 4 or 5.

Example 1

Synthesis of Ethylene Glycol Oligolactide with Terminal Isocyanate Groups (EOL-NCO)

33 g (0.094 mol) of the oligo ester ethylene glycol oligolactide (EOL) were reacted with 31.6 g (0.188 mol) of hexamethylene diisocyanate (HMOI) for 4 hours at 50° C. under argon. The reaction mixture was then stirred at 50° C. for 2 days. A colorless, water-insoluble, viscous oil was obtained as the reaction product, which displayed a strong isocyanate band at 2266 cm$^{-1}$ in the IR spectrum. NMR spectrometry also performed confirmed the presence of the reaction product EOL-NCO.

Example 2

Rheological Studies for the Determination of the Viscosity and the Gel Point 2.1 Viscosity The rheological studies on the viscosity of the adhesive prepolymer EOL-NCO and the crosslinking partner used Protasan UPCI 213 (medical grade, $M_w$=270 kDa, 4% in $H_2O$, FMC Biopolymers Drummen Norway) were performed on the rheometer Rheostrese® 1 from Thermo Haake under the following measurement conditions: measurement system plate-plate (diameter 20 mm), measurement gap 1 mm, oscillation test, measurement mode CS (controlled stress=shear stress preset), measurement procedure time-sweep, test parameters: shear stress=5 Pa, frequency f=1 Hz, temperature T=37° C. The applied volume of the particular adhesive components to be measured was 700 µl. The complex dynamic viscosity $|\eta^*|=[Pa \cdot s]$ was determined for each adhesive component. The values for $|\eta^*|$ after 300 s and 600 s shown in Table 1 are mean values which are each obtained from 3 individual measurements.

TABLE 1

Complex dynamic viscosity of the adhesive components studied

|  | Viscosity $|\eta^*|$ [Pa · s] | |
| --- | --- | --- |
| Adhesive component | at t = 300 s | at t = 600 s |
| EOL-NCO (EOL/HMDI, 1/2 n/n) | 261.7 ± 9.9 | 250.1 ± 8.8 |
| EOL-NCO (EOL/HMDI, 1/3 n/n) | 2.0 ± 0.02 | 2.0 ± 0.03 |
| EOL-NCO (EOL/HMDI, 1/2 n/n)/ DMSO (89/11 w/w) | 36.7 ± 3.0 | 35.7 ± 2.9 |
| EOL-NCO (EOL/HMDI, 1/2 n/n)/ DMSO (85/15 w/w) | 5.8 ± 0.2 | 5.8 ± 0.2 |
| EOL-NCO (EOL/HMDI, 1/2 n/n)/ DMSO (85/15 w/w), γ-sterilized (>25 kGy) | 8.6 ± 0.4 | 8.8 ± 0.7 |
| Protasan UPCI 213 ($M_w$ = 270 kDa, 4% in $H_2O$) | 6.7 ± 0.3 | 7.8 ± 0.5 |
| Protasan UPCI 213 ($M_w$ = 270 kDa, 4% in $H_2O$), steam sterilized (121° C., 20 min) | 5.1 ± 0.5 | 6.6 ± 0.6 |
| Protasan UPCI 213 (4% in $H_2O$), γ-sterilized (>25 kGy) | <0.5 | <0.5 |

Since with application via two-chamber syringes for optimal mixing the two adhesive components should display a similar viscosity, the viscosity of the crosslinking partners was adapted to that of the EOL-NCO, made up with DMSO. After γ-sterilization, a marked decrease in the solution viscosity was observed as a result of chain degradation. Viscosities comparable with EOL-NCO (EOL/HMDI, 1/2 n/n)/ DMSO (85/15 w/w) were obtained with Protasan UPCI 213 after steam sterilization. Hence, in the further studies, only steam-sterilized Protasan UPCI 213 solutions were used.

2.2 Gel Point

To be able to assess the workability of the liquid adhesive components as a two-component system, the gel point was determined with the rheometer Rheostress® 1 from Thermo Haake. The gel point is defined as the sol/gel transition point at which the storage modulus (elastic fraction) G' is equal to the loss modulus G" (viscous fraction). It characterizes the transition from liquid behavior (G">G') to gel-like or solid behavior (G'>G"). The following measurement conditions were used for the gel point determination: measurement system plate-plate (diameter 20 mm), measurement gap 1 mm, oscillation test, measurement mode CD (controlled deformation=deformation preset), measurement procedure time-sweep, test parameters: deformation γ=0.1, frequency f=5 Hz, temperature T=37° C., duration t=2000 s, applied volume: 1 ml.

The gel point was determined on the basis of the intersection point of the moduli from 5 measurements after mixing of EOL-NCO (EOL/HMDI 1/2 n/n)/DMSO (85/15 w/w, γ-sterilized >25 kGy) and Protasan UPCI 213 (medical grade $M_w$=270 kDa, 4% in $H_2O$, steam-sterilized 121° C., 20 min) and compared with the fibrin adhesive (Tissucol duo S Immuno, Baxter Deutschland GmbH, Unterschleissheim).

Figure 3:
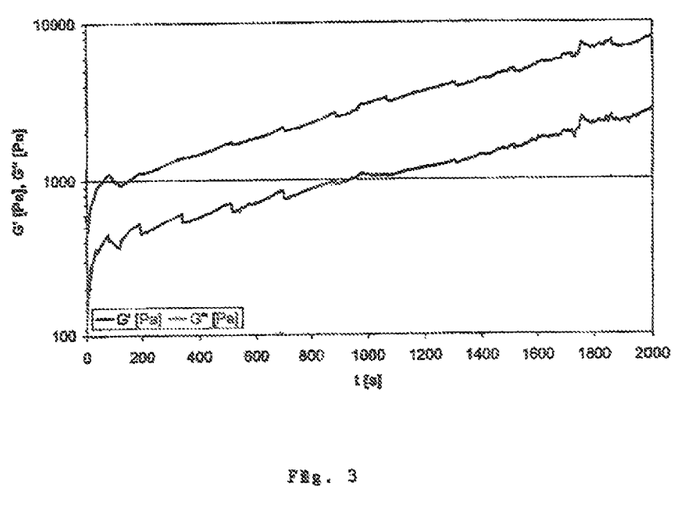
FIG. 3: dynamic studies for the determination of the gel point of a fibrin adhesive (plotting of the storage modulus G' [Pa] and loss modulus G" [Pa] against time t [s])
Figure 4:
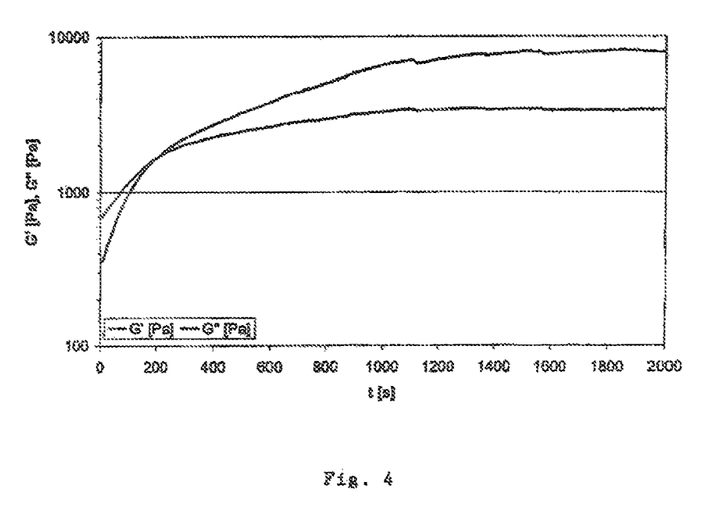
FIG. 4: dynamic studies for the determination of the gel point on a combination (EOL-NCO (γ-sterilized)/Protasan UPCI 213 (steam-sterilized), plotting of the storage modulus G' [Pa] and loss modulus G" [Pa] against time t [s])

The measurements showed that the fibrin adhesive reaches its gel point immediately and was not metrologically determinable with the Rheometer. This was highlighted by the fact that right at the start of measurement G'>G" (FIG. 3). In contrast, the sol/gel transition of EOL-NCO (EOL/HMDI 1/2 n/n)/DMSO (85/15 w/w)/Protasan UPCI 213 ($M_w$=270 kDa, 4% in $H_2O$) lay at 196.4±40.1 s (FIG. 4). The delayed pot or gel time of the combination compared to fibrin adhesive has the advantage for the user that after application of the combination an adequate processing time is still available, for example, for the fixing of the tissue parts or bone fragments to be adhesively bonded and/or for positioning or repositioning of defect-covering materials. The high viscosity of the individual components of the combination prevents the components from flowing out of the wound or away from the application site or from being flushed out of the wound area in the case of heavily bleeding or heavily exuding wounds.

Example 3

Ca. 4 g of Protasan UPCI 213 (FMC Biopolymers, Drammen Norway) were dissolved in 100 ml of water. The solution was then sterilized at ca. 121° C. for 20 mins by steam sterilization. After the sterilization, the molecular weight of the chitosan was determined by means of GPC (gas pressure chromatography). The molecular weight was ca. 216 kDa. The viscosity of the sterile 4 wt. % Protasan solution was ca. 1.99 Pa·s.

Example 4

A mixture of ethylene glycol oligolactide which is modified at its ends by reaction with hexamethylene diisocyanate (HMDI) and DMSO was sterilized with γ radiation (>25 kGy). However, it could be shown by NMR studies that the chemical structure of the ethylene glycol oligolactide end-capped with HMDI was retained.

Example 5

Testing of the Strength of the Adhesive Joint to Soft Tissue

The mechanical testing of the adhesive joint was performed under uniaxial tensile stress on the Zwick BZ2.5/ TN1S universal test machine (Zwick GmbH & Co, KG, Germany; load cell 50 N). For the testing of the adhesive bonds, the soft tissue parts, in this case parts of bovine muscle tissue, were fixed in polymethyl methacrylate (PMMA) interlocking sample clamps. To create a comparable reference area for the bonding, the clamped soft tissue samples were cut to an average size of 230 $mm^2$. Next, after manual mixing in a vial, 200 µl of the adhesive system to be tested was applied onto the tissue. The prepared soft tissue pieces were held at a defined pressure of 2 N for 10 minutes at room temperature (23° C.) or 37° C. in the universal test machine and then pulled apart at a test speed of 10 mm/min with measurement of the force-distance ratio and the adhesive strength was determined with respect to the reference area.

Figure 5:
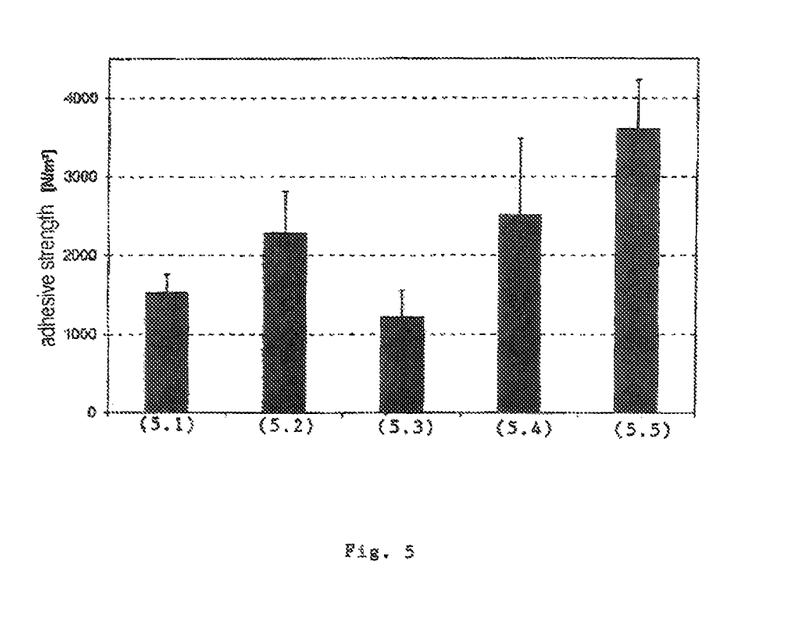
FIG. 5: adhesive strength of various adhesive systems, including combinations on bovine muscle tissue at room temperature (the adhesive strength [N/m$^2$] is plotted on the y-axis and the adhesive system studied on the x-axis)

5.1 Implementation of the Bonding Reaction for Soft Tissue Bonding at Room Temperature (23° C.) after Manual Mixing The adhesive strength [N/$mm^2$] of the following adhesive systems was tested in serial tests at room temperature: (5.1) without addition of adhesive; (5.2) fibrin (Tissucol duo S Immuno, Baxter Deutschland GmbH, Unterschleissheim); (5.3) EOL-NCO (EOL/HMDI 1/2 n/n)/DMSO (85/15 w/w, component 1) and $H_2O$ (component 2); (5.4) EOL-NCO (EOL/HMDI 1/3 n/n, component 1) and Protasan UPCI 213 ($M_w$=270 kDa (g/mol), 4% in $H_2O$, component 2); and (5.5) EOL-NCO (EOL/HMDI 1/2 n/n)/DMSO (85/15 w/w, component 1) and Protasan UPCI 213 ($M_w$=270 kDa, 4% in $H_2O$, component 2). The mean values for the adhesive strengths, each from 12 individual tests, are plotted in FIG. 5.

Figure 6:
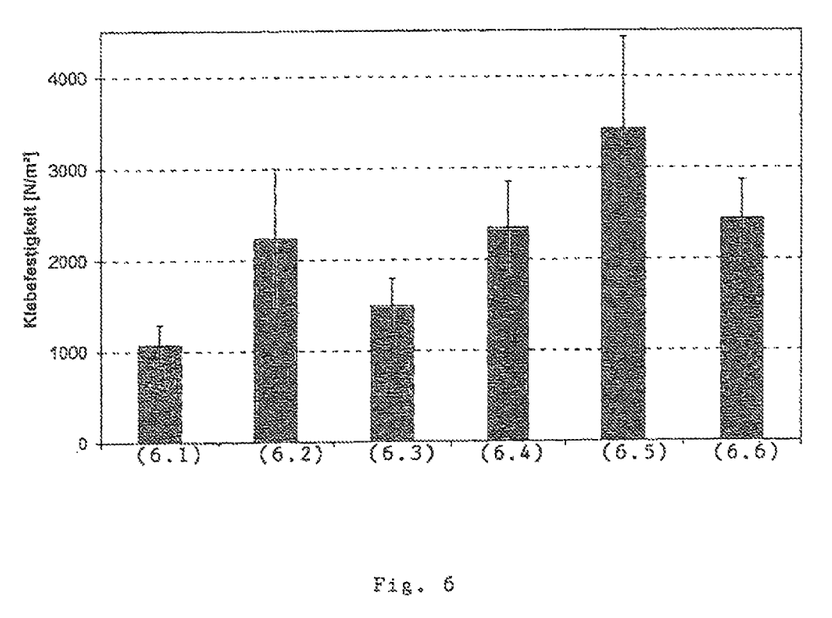
FIG. 6: adhesive strength of various adhesive systems, including combinations, on bovine muscle tissue at 37° C. (n=12 tests each time, the adhesive strength [N/m$^2$] is plotted on the y-axis and the adhesive system studied on the x-axis)

5.2 Implementation of the Bonding Reaction for Soft Tissue Bonding at 37° C. after Manual Mixing To be able to study the adhesive action at body temperature, further tests were performed at 37° C. For this, the soft tissue pieces clamped in the PMMA holders and packed in foil were conditioned for one hour at 37° C. by storing in the warming cabinet before the tests. Moreover, the universal test machine was equipped with a thermostatted conditioning chamber ($\Delta\theta$=0.5° C.), so that the tensile test could take place at 37° C. Thus, the test series already performed at room temperature were repeated for the determination of the adhesive strength to soft tissue at 37° C.: (6.1) without addition of adhesive; (6.2) fibrin (Tissucol duo S Immuno, Baxter Deutschland GmbH, Unterschleissheim); (6.3) EOL-NCO (EOL/HMDI 1/2 n/n)/DMSO (85/15 w/w, component 1) and $H_2O$ (component 2); (6.4) EOL-NCO (EOL/HMDI 1/3 n/n, component 1) and Protasan UPCI 213 ($M_w$=270 kDa, 4% in $H_2O$, component 2) and (6.5) EOL-NCO (EOL/HMDI 1/2 n/n)/DMSO (85/15 w/w, component 1) and Protasan UPCI 213 ($M_w$=270 kDa, 4% in $H_2O$, component 2). In addition, the content of the solvent DMSO was varied, so as to result in the adhesive variant (6.6) with EOL-NCO (EOL/HMDI 1/2 n/n)/DMSO (89/11 w/w, component 1) and Protasan UPCI 213 (4% in $H_2O$, component 2). The mean values for the individual test series (n=12) are shown in FIG. 6.

Figure 7:
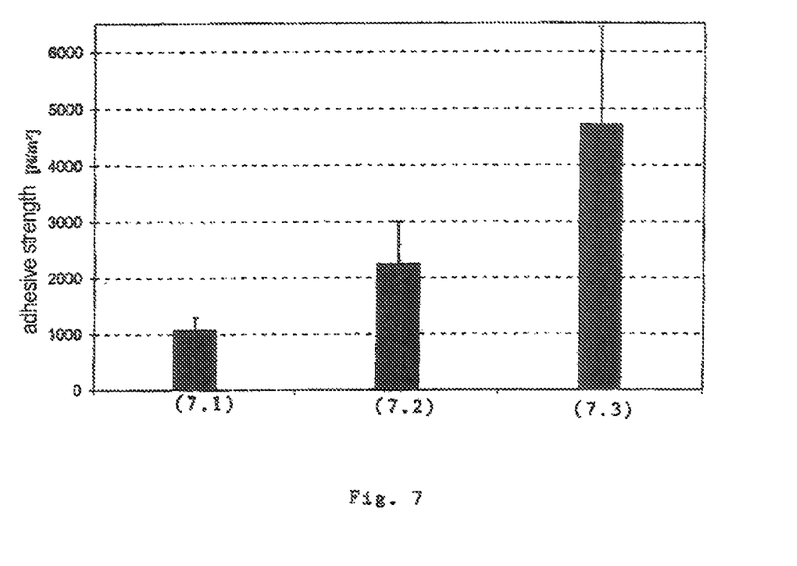
FIG. 7: adhesive strength of various adhesive systems, including combinations, on bovine muscle tissue at 37° C. (the adhesive strength [N/m$^2$] is plotted on the y-axis and the adhesive system studied on the x-axis, n=12 tests each time)

5.3 Implementation of the Bonding Reaction for Soft Tissue Bonding at 37° C. with the Use of Two-Chamber Syringes with Sterilized Adhesive Components To create normal practical use conditions, the sterilized adhesive components were administered in two-chamber syringes with static mixers (Mixpac Systems AG, Rotkreuz, Switzerland, chamber ratio 1:1). For the tests, the system EOL-NCO (EOL/HMDI 1/2 n/n)/DMSO (85/15 w/w, γ-sterilized >25 kGy) as component 1 and Protasan UPCI 213 (medical grade, $M_w$=270 kDa, 4% in $H_2O$, steam-sterilized 121° C., 20 min) as component 2 (7.3) was applied together. As references, the fibrin adhesive (Tissucol duo S Immuno, Baxter Deutschland GmbH, Unterschleissheim (7.2)) and tissue samples without addition of adhesive (7.1) were used. The adhesive strength was determined from 12 individual tests for each (FIG. 7).

Figure 8:
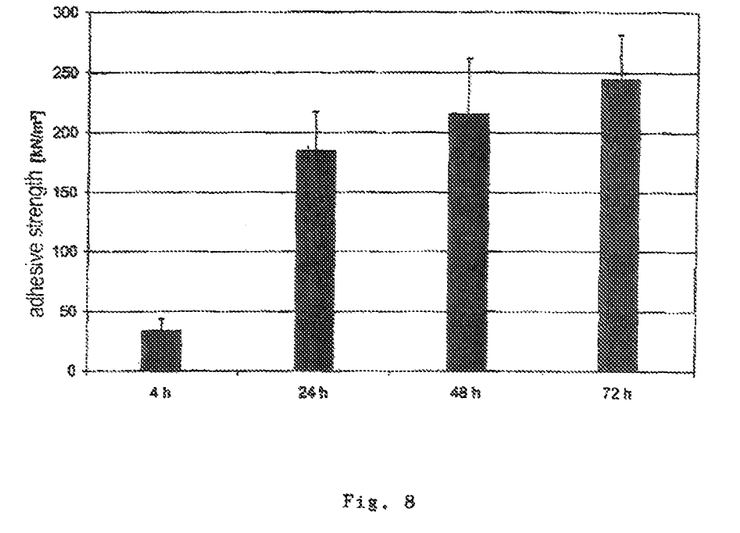
FIG. 8: adhesive strength of a combination on a polyurethane hard foam at 37° C. after 4 h, 24 h, 48 h and 72 h (the adhesive strength [KN/m$^2$] is plotted on the y-axis and the time [h] on the x-axis, n=12 tests each time).

5.4 Implementation of the Bonding Reaction for Hard Tissue Bonding at 37° C. with the Use of Two-Chamber Syringes with Sterilized Adhesive Components For the assessment of the bonding strength of the synthesized adhesive system on hard tissue, the test arrangement was modified. As the hard tissue model material, an open-celled polyurethane hard foam with pore sizes of 500-1200 μm, which had been further processed into square test piece plates with geometry 15 mm×15 mm×3 mm with a diamond wire saw (Histo-Saw DDM-P216, Medim) was used. The disposable test pieces thus obtained were then cleaned with 99% ethanol in the ultrasonic bath and fixed on the square PMMA holders with cyanoacrylate for the recording in the universal test machine. The sterilized adhesive components were also applied onto the fixed polyurethane plates using two-chamber syringes with static mixer (Mixpac Systems AG, Rotkreuz, Switzerland, chamber ratio 1:1). Next the sample pair was lightly pressed together and stored packed in the moist environment at 37° C. for 4 h, 24 h, 48 h and 72 h. The testing of the strength of the adhesive joint was performed under uniaxial tensile stress on the Zwick BZ2.5/TN1S universal test machine (Zwick GmbH & Co, KG, Germany; load cell 500 N) without application of a defined initial force, at a test speed of 5 mm/min. FIG. 8 shows the mean value from the measurement series after 4 h, 24 h, 48 h and 72 h (n=12 for each) for EOL-NCO (EOL/HMDI 1/2 n/n)/DMSO (85/15 w/w, γ-sterilized >25 kGy) and Protasan UPCI 213 (medical grade, $M_w$=270 kDa, 4% in $H_2O$, steam-sterilized 121° C., 20 min). The experiment showed that the adhesive strength of the adhesive increases after application, which is particularly advantageous for bone bonding and/or for the treatment of bone defects.

5.5 Implementation of the Bonding Reaction for Hard Tissue Adhesive Bonding after Water Storage at 37° C.

The effect of a moisture input (for example, because of hemorrhage) on the polymerization process and the bonding strength of the adhesive system EOL-NCO (EOL/HMDI 1/2 n/n)/DMSO (85/15 w/w, γ-sterilized >25 kGy) and Protasan UPCI 213 (medical grade, $M_w$=270 kDa, 4% in $H_2O$, steam-sterilized 121° C., 20 min) was simulated by storage of prepared polyurethane hard foam samples in distilled water at 37° C. The polyurethane hard foam samples were prepared analogously to Example 5.4 described above and after prestorage at 37° C. in the moist environment for 10 min, 2 h and 24 h, respectively, were conditioned in a waterbath at 37° C. for a further 24 h. The adhesive strengths measured after the respective storage times had elapsed confirm that the adhesive strength of the combination is essentially not affected by moisture (concerning this, compare the values reproduced in Table 2 with the adhesive strengths illustrated in FIG. 7).

TABLE 2

Bonding strength of EOL-NCO (EOL/HMDI 1/2 n/n)/DMSO (85/15 w/w, γ-sterilized) and Protasan UPCI 213 (steam-sterilized) on polyurethane hard foam at 37° C. after 10 min, 2 h and 24 h prestorage in the moist environment followed by water storage for 24 h (n = 2 tests each time).

| Prestorage | Adhesive strength [kN/m²] |
|---|---|
| 10 min | 196.9 |
|  | 222.9 |
| 2 h | 234.7 |
|  | 243.6 |
| 24 h | 212.7 |
|  | 235.5 |

5.6 Modification of the Adhesive System for Hard Tissue Adhesive Bonding

For the use of the adhesive system as a hard tissue adhesive, it is desirable to achieve an osteoinductive action by means of fillers. For this, as well as calcium phosphates such as for example, hydroxylapatite and β-tricalcium phosphate, carbonates, for example, calcium carbonate, or oxide materials, for example, silicon dioxide, are possible. On the basis of the structure of spongy bone components, a particle size distribution of the fillers between 20 nm and 1 μm, preferably 20 nm and 100 nm, is advantageous for this. In this connection, the suitability of EOL-NCO (EOL/HMDI 1/2 n/n)/DMSO (85/15 w/w, γ-sterilized) and Protasan UPCI 213 (steam-sterilized) as hard tissue adhesives in combination with fillers was studied. No effect of the filler on the bonding strength could be observed at a filler content of 5%. This was verified on the basis of 3 tests on a polyurethane hard foam as the substrate to be bonded.

Example 6

Bovine muscle meat was cut into rectangular pieces with a base area of cal 2 cm². The cut pieces were conditioned at ca.

37° C. and clamped into the two clamping jaws of a tensile test machine from Zwick (Ulm, Germany). The sterile Protasan solution (see Example 1) and the sterile solution of the EOL isocyanate in DMSO (see Example 2) were placed in a sterile two-chamber syringe beforehand and combined using a static mixing syringe. Next, ca. 200 µl of the pasty composition formed thereby was applied onto the meat piece in the lower clamping jaw. The two pieces of meat were pressed together with an initial load of ca. 2 Newtons for ca. 10 minutes, before the bonding strength of the tissue adhesive was determined at a speed of ca. 10 mm/min. In a control experiment, pieces of meat were adhesively bonded with ca. 200 µl of fibrin adhesive (Baxter). In a further control experiment, pieces of meat were pressed together without adhesive. The results from 12 measurements are presented in Table 3 below. These show that an adhesive resulting from the combination displays markedly stronger bonding strength compared to the fibrin adhesive.

TABLE 3

|  | Bonding strength [N/m$^2$] | Standard deviation |
| --- | --- | --- |
| EOL isocyanate-chitosan | 3705 | 962 |
| Fibrin adhesive | 1652 | 366 |
| Without adhesive | 781 | 296 |

Example 7

Finally, analogously to Example 3, the adhesive bonding of porcine liver tissue was studied. The results are listed in Table 4 below.

TABLE 4

|  | Bonding strength [N/m$^2$] | Standard deviation |
| --- | --- | --- |
| EOL isocyanate-chitosan | 1308 | 664 |
| Fibrin adhesive | 553 | 320 |
| Without adhesive | 118 | 33 |

Example 8

In a further experiment, muscle meat pieces were subjected to a tensile test with EOL-NCO-chitosan analogously to Example 3. After determination of the bonding strength, the meat pieces were again pressed together for 10 minutes. Then the force to be applied to pull the meat pieces apart was again determined. In a total of 12 tests, the absolute bonding strength differed from the initially determined bonding strength by less than 20%. Identical tests were performed with the fibrin adhesive mentioned in Example 3. In this, bonding strength could no longer be detected after renewed pressing together of the meat pieces. The bonding property of the combination after mixing of the components thereof described in this example is of great importance particularly in the fixing of bone fractures, wherein after an initial adhesive bonding of the bone parts to be joined, corrections by the surgeon can become necessary in the further course of the treatment.

Example 9

In Vitro Studies on a Biological Tissue

The pressure resistance of a combination (EOL isocyanate solution in 80/20 DMSO (w/w) and a 4% Protasan solution) was determined with a cylindrical biosimulator. The biosimulator used with a pressure-resistant casing is 400 mm high and has a diameter of 150 mm. The lid with holder for clamping of biological tissue has a circular hole with a diameter of 30 mm. Prepared, moist bovine pericardium was cut into 60 mm×60 mm pieces and dabbed dry. A circular defect with a diameter of 10 mm was created centrally with a hole punch and the pericardium was introduced into the holder of the cylindrical lid. The piece punched out beforehand was adhesively bonded onto the created defect using the combination. After a curing time of 120 s, an overpressure was created in the biosimulator using air pressure, and the maximal overpressure up to tearing of the bonding site was detected. With n=5 measurements, a mean overpressure of 74.3 mbar could be determined. In a further experiment, a maximal overpressure of 50 mbar was set, and the pressure was maintained for 1 min and then released. This procedure was repeated 30 times, without the adhesively bonded joint tearing.

The experiment demonstrates the pressure resistance and elasticity of the adhesively bonded joint on biological tissue. Hence, the combination is, for example, suitable for the closure of air leakages such as can, in particular, arise in the lung after resection procedures.

Example 10

Toxicological Studies

A sterile EOL isocyanate solution in 80/20 DMSO (w/w) was mixed with a 4% Protasan solution using a Mixpac mixer syringe and subjected to a cytotoxicity test according to ISO 10993 (Biological Evaluation of Medical Devices Part 5: Test for Cytotoxicity). In the assessment of the test, the EOL isocyanate-Protasan mixture was given the score 0=no reactivity (discrete intracytoplasmic, no cell lysis) as was the negative control, while the positive control run in parallel displayed cytotoxic properties with the score 4=severe reaction (nearly complete destruction of the cell layers).

Example 11

Staunching of Liver Hemorrhages

In a further experiment, the combination was used for the stoppage of liver hemorrhages in rabbits. After anaesthetization of the animals, a laparotomy was performed, the liver laid open and a partial resection performed on one hepatic lobe in each. The hemorrhaging liver was treated with the combination, the components thereof (in this case a 4 wt. % Protasan solution and a mixture of EOL isocyanate and DMSO (80/20 w/w) being mixed on the liver wound. In all the rabbits, the hemorrhages could be stopped in less than 60 seconds.

Example 12

Staunching of Abrasions

A sterile EOL isocyanate compound-DMSO mixture 80/20 (w/w) and a sterile 3% (w/v) Protasan solution were placed in a two-chamber applicator with attached spray system. Using emery paper on the skin of anesthetized rats a 4×4 cm abrasion was created, onto which the aforesaid combination was applied with three successive plunger strokes. A homogeneous film which completely covered the wound was formed on the wound surface.

Example 13

Intestinal Leakages in the Pig

After anaesthetization, several punctures in the colon of a pig were made with a pointed cannula. A sterile EOL isocyanate solution in 80/20 DMSO (w/w) was mixed with a 4% Protasan solution using a Mixpac mixing syringe and applied to the puncture sites. The milky-white turbidity makes it easier for the surgeon to apply the adhesive accurately onto the tissue. In parallel, puncture sites were also treated with a pure viscous EOL isocyanate solution or with a pure 4% chitosan solution. After a curing time of 180 s, the airtightness of the puncture was tested by compression of the intestine. As a result, the puncture sites treated with the combination were found to be airtight or sealed, while the puncture sites treated with a pure EOL isocyanate solution or pure 4% chitosan solution were not airtight, as could seen from the escaping air bubbles.

Example 14

Puncture Channel Hemorrhages

After anesthetization of the pigs (n=3) and opening of the abdomen, the infrarenal aorta was laid open. A ca. 3 cm long vascular section was explanted and replaced by a PTFE prosthesis in an "end to end anastomosis." On opening of the vascular clamps, puncture channel hemorrhages were to be seen at both anastomoses, which after renewed application of the vascular clamps were treated with a combination (EOL isocyanate solution in 80/20 DMSO (w/w) and 4% Protasan solution). Here, the milky-white turbidity of the mixture obtained made it easier for the surgeon to apply the adhesive accurately onto the tissue. The vascular clamps were again opened 30 s after application of the combination. No more puncture channel hemorrhages occurred.

The animal experiments described above demonstrate the functionality of the combination for the closure of liquid and air leakages. The milky-white turbidity produced on mixing of the components a) and b) of the combination makes it easier for the surgeon to distinguish between combination and tissue to be treated, as a result of which the combination can particularly advantageously be applied accurately.

The invention claimed is:

1. A composition for adhesive bonding and/or fixing of biological and/or synthetic tissues comprising:
   a) a nitrogen-functionalized polysaccharide; and
   b) a terminally functionalized oligolactone having terminal isocyanate groups.

2. The composition as claimed in claim 1, wherein the polysaccharide is a naturally occurring polysaccharide.

3. The composition as claimed in claim 1, wherein the polysaccharide is a polysaccharide bearing amino groups.

4. The composition as claimed in claim 1, wherein the content of monosaccharide units in the polysaccharide which bear an amino group is at least 30%, preferably 80%.

5. The composition as claimed in claim 1, wherein the polysaccharide is an at least partly deacetylated glycosaminoglycan (mucopolysaccharide).

6. The composition as claimed in claim 1, wherein the polysaccharide has a deacetylation level between 50 and 98%.

7. The composition as claimed in claim 1, wherein the polysaccharide is chitosan or a derivative thereof.

8. The composition as claimed in claim 1, wherein the oligolactone is formed from a polyhydric alcohol and hydroxycarboxylic acids.

9. The composition as claimed in claim 1, wherein the content of polysaccharide in the combination is 1 to 80wt %.

10. The composition as claimed in claim 1, wherein the content of oligolactone in the combination is 20 to 99 wt %.

11. The composition as claimed in claim 1, wherein the polysaccharide and/or the oligolactone are dispersed or dissolved in one or more solvents.

12. The composition as claimed in claim 1, wherein the polysaccharide is present as an aqueous solution with a polysaccharide content of 2 to 5 wt %, based on the total weight of the solution.

13. The composition as claimed in claim 1, wherein the oligolactone is present as a DMSO solution with an oligolactone content between 50 and 99 wt %, based on the total weight of the solution.

14. The composition as claimed in claim 1, wherein the polysaccharide and/or the oligolactone are present separately from one another in chambers of a Multicomponent syringe.

15. The composition as claimed in claim 1, wherein the crosslinking reaction of the components is initiated within a period of <1000 seconds after mixing thereof on a substrate to be adhesively bonded.

16. The composition as claimed in claim 1, wherein the combination contains collagen, gelatin and/or albumin as additives.

17. The composition as claimed in claim 1, wherein the polysaccharide and/or the oligolactone are present in sterilized form.

18. The composition as claimed in claim 1, wherein the combination is an adhesive composition.

19. A compound comprising the composition as claimed in claim 1, wherein the polysaccharide is at least partly crosslinked with the oligolactone.

20. A medical equipment product comprising the composition as claimed in claim 1.

21. An in vitro process for adhesive bonding comprising:
    contacting components of the composition as claimed in claim 1 with one another and with at least one substrate to be bonded, wherein said oligolactone contains reactive functional groups.

* * * * *